United States Patent
Miller et al.

(10) Patent No.: US 10,065,198 B2
(45) Date of Patent: Sep. 4, 2018

(54) CENTRIFUGE LOADING APPARATUS, SYSTEMS, AND METHODS

(71) Applicant: Siemens Healthcare Diagnostics Inc., Tarrytown, NY (US)

(72) Inventors: Kerry Miller, Elkton, MD (US); Steven Sparks, Wilmington, DE (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 364 days.

(21) Appl. No.: 14/774,344

(22) PCT Filed: Mar. 10, 2014

(86) PCT No.: PCT/US2014/022485
§ 371 (c)(1),
(2) Date: Sep. 10, 2015

(87) PCT Pub. No.: WO2014/164459
PCT Pub. Date: Oct. 9, 2014

(65) Prior Publication Data
US 2016/0016183 A1    Jan. 21, 2016

Related U.S. Application Data

(60) Provisional application No. 61/776,100, filed on Mar. 11, 2013.

(51) Int. Cl.
*B04B 5/10* (2006.01)
*B04B 9/14* (2006.01)
(Continued)

(52) U.S. Cl.
CPC .......... *B04B 11/043* (2013.01); *B04B 5/0414* (2013.01); *B04B 5/10* (2013.01);
(Continued)

(58) Field of Classification Search
CPC ........ B04B 5/10; B04B 13/00; B04B 5/0407; B04B 9/00; B04B 5/0421; B04B 5/0414;
(Continued)

(56) References Cited

U.S. PATENT DOCUMENTS 3,151,073 A * 9/1964 Anthon ............ B04B 5/04
198/803.9
3,644,095 A * 2/1972 Netheler ............ G01N 35/0092
141/130
(Continued)

FOREIGN PATENT DOCUMENTS

JP    2004230328 A * 8/2004    ........... B04B 5/0421
JP    2004230329 A * 8/2004    ........... B04B 5/0421
(Continued)

OTHER PUBLICATIONS

Machine Translation from WIPO of WO 2012/090795 to Yagi et al. (Year: 2012).*
(Continued)

*Primary Examiner* — Charles Cooley

(57) ABSTRACT

A loading apparatus and system is adapted to load unprocessed sample containers in a centrifuge and provide improved balance thereof. The apparatus has a staging platform containing at least two bucket inserts, a weight scale operable to determine a combined weight of each of the bucket inserts, a centrifuge configured to receive the bucket inserts as pairs, a robot operable to insert an unprocessed sample container into the bucket inserts, and a controller operable to command the robot to carry out placement of the unprocessed sample container into a highest priority empty receptacle of a lowest combined weight bucket insert. Methods of operating the system are provided.

20 Claims, 6 Drawing Sheets

(51) Int. Cl.
  *B04B 13/00* (2006.01)
  *B04B 11/04* (2006.01)
  *B04B 5/04* (2006.01)
  *B25J 11/00* (2006.01)
  *G01N 35/00* (2006.01)

(52) U.S. Cl.
  CPC .............. *B04B 9/14* (2013.01); *B04B 13/00* (2013.01); *B25J 11/00* (2013.01); *B04B 2011/046* (2013.01); *G01N 2035/00495* (2013.01)

(58) Field of Classification Search
  CPC ....... B04B 2011/046; B04B 9/10; B04B 5/00; B04B 9/14; B04B 2009/143; G01N 35/04; G01N 35/00; G01N 2035/0465; G01N 35/02; G01N 35/0092; G01N 2035/00495; G01N 2035/0094
  See application file for complete search history.

(56) References Cited

U.S. PATENT DOCUMENTS

| | | | | |
|---|---|---|---|---|
| 5,623,415 | A * | 4/1997 | O'Bryan | G01N 35/021 198/617 |
| 5,674,322 | A * | 10/1997 | Kunz | B04B 5/10 127/53 |
| 5,721,676 | A * | 2/1998 | Bolden | A61M 1/387 422/72 |
| 5,740,185 | A * | 4/1998 | Bosse | G11B 20/1833 356/39 |
| 5,814,276 | A * | 9/1998 | Riggs | G01N 35/04 422/549 |
| 5,865,718 | A * | 2/1999 | Chan | B04B 13/00 494/10 |
| 6,060,022 | A | 5/2000 | Pang et al. | |
| 6,461,287 | B1 * | 10/2002 | Glater | B01D 3/08 159/DIG. 11 |
| 7,025,714 | B2 | 4/2006 | Escal | |
| 7,195,737 | B2 * | 3/2007 | Itoh | B04B 5/0421 422/65 |
| 8,617,041 | B2 * | 12/2013 | Haechler | B04B 13/00 422/72 |
| 8,795,144 | B2 * | 8/2014 | Pedrazzini | B04B 5/0421 494/20 |
| 2004/0022682 | A1 * | 2/2004 | Itoh | G01N 35/04 422/64 |
| 2004/0089737 | A1 * | 5/2004 | Itoh | B04B 5/0421 239/264 |
| 2004/0102920 | A1 * | 5/2004 | Itoh | B04B 5/0414 702/173 |
| 2004/0184958 | A1 * | 9/2004 | Itoh | B04B 5/0421 422/72 |
| 2004/0184959 | A1 * | 9/2004 | Itoh | B04B 5/0421 422/72 |
| 2007/0020764 | A1 * | 1/2007 | Miller | G01N 35/0092 436/45 |
| 2007/0059209 | A1 * | 3/2007 | Pang | G01N 35/0095 422/72 |
| 2009/0003981 | A1 * | 1/2009 | Miller | B65G 1/04 414/267 |
| 2009/0047179 | A1 * | 2/2009 | Ping | G01N 35/0095 422/72 |
| 2009/0275458 | A1 * | 11/2009 | Dee | G01N 35/0095 494/10 |
| 2009/0318276 | A1 * | 12/2009 | Miller | B04B 13/00 494/20 |
| 2011/0045958 | A1 * | 2/2011 | Pedrazzini | B04B 5/0421 494/8 |
| 2011/0245061 | A1 * | 10/2011 | Haechler | B04B 13/00 494/8 |
| 2012/0129673 | A1 * | 5/2012 | Fukugaki | C01N 35/00029 494/1 |
| 2013/0307381 | A1 * | 11/2013 | Itoh | G01N 35/04 312/97 |
| 2015/0111299 | A1 * | 4/2015 | Watabe | G01N 35/0095 436/45 |
| 2015/0141232 | A1 * | 5/2015 | Verweij | B04B 5/10 494/16 |
| 2015/0360239 | A1 * | 12/2015 | Yang | B04B 13/00 494/10 |
| 2016/0016183 | A1 * | 1/2016 | Miller | B04B 5/0414 494/1 |
| 2016/0023220 | A1 * | 1/2016 | Miller | B04B 5/0414 494/16 |
| 2017/0021367 | A1 * | 1/2017 | Itoh | B04B 5/0407 |
| 2017/0219616 | A1 * | 8/2017 | Pedrazzini | G01N 35/00009 |

FOREIGN PATENT DOCUMENTS

| | | | |
|---|---|---|---|
| JP | 2011056397 A * | 3/2011 | ............... B04B 5/10 |
| JP | 2011189324 A * | 9/2011 | ............ B04B 13/00 |
| WO | 2012/090795 A1 | 7/2012 | |

OTHER PUBLICATIONS

PCT International Search Report and Written Opinion dated Jul. 15, 2014 (8 Pages).

* cited by examiner

CENTRIFUGE LOADING APPARATUS, SYSTEMS, AND METHODS

CROSS-REFERENCE TO RELATED APPLICATIONS

This application claims priority to U.S. Provisional Application Ser. No. 61/776,100 filed Mar. 11, 2013, which is incorporated herein by reference in its entirety.

FIELD

The present invention relates generally to methods of automated loading and unloading of a centrifuge.

BACKGROUND

In medical testing and processing, the use of robotics may minimize exposure to, or contact with, bodily fluid samples (otherwise referred to as "specimens") and/or may increase productivity. For example, in some existing automated testing and processing systems (e.g., centrifuges), sample containers (such as blood collection tubes or the like) may be transported from an automated conveyor system by a transfer robot, and placed in an incoming bucket insert located within an incoming staging area. Bucket inserts are multi-receptacle containers that have numerous receptacles (e.g., 20 or more receptacles) adapted to receive sample containers. Incoming bucket insert, once filled, is then transported from the input staging area to a bucket of the centrifuge. This process is continued until the buckets of the centrifuge are appropriately filled, as desired.

The specimens are then centrifuged by spinning at high RPM to separate the whole blood and serum components (e.g., blood components). The time needed for full centrifuging may be between about 8-12 minutes. Once centrifugation is complete, the bucket inserts are moved by a robot to an outgoing staging area, and a transfer robot then may proceed to empty the outgoing bucket insert and place the samples back onto the automated conveyor system.

Typically, the incoming staging area includes a weight scale for obtaining the weights of the incoming bucket inserts and sample containers provided therein. Various methods have been used for attempting to equalize the weights of the various pairs of bucket inserts so that unbalance of the centrifuge is minimized. For example, in a simple method, one or more weights from a set of dummy weight tubes (e.g., containing water) is placed in one or more receptacles of one of the buckets of the bucket insert pair to approximately balance the centrifuge. In another method, weight balancing is accomplished by inserting the sample containers into the bucket insert pairs in a predetermined pattern. Weight adjustments may take place via moving sample containers between receptacles of the bucket insert pairs to obtain better balance of the pairs. In another method, weight balancing is accomplished during loading wherein sample containers are placed into bucket insert pairs based upon a known weight of each bucket insert and its current contents and an "estimated" weight of the sample container to be placed which is based upon an average weight estimate determined based upon a measured height and diameter of the sample container. In this instance, the sample container is always placed in the bucket insert of the pair having the lowest weight at that time.

Although existing methods may provide suitable efficiencies, balancing steps after placement or reconfiguring sample containers to attain better balance adds process time and detracts from efficiencies. Methods based upon average estimates are inherently not accurate. Accordingly, more efficient methods of balancing the centrifuge are sought so as to further reduce both processing time and cost. Accordingly, systems and methods that may improve balancing of centrifuges are desired.

SUMMARY

According to a first aspect, an improved method of loading a centrifuge is provided. The method includes determining weights of bucket inserts, and placing an unprocessed sample container into a highest priority unoccupied receptacle location of a lowest weight bucket insert.

In a system aspect, a centrifuge loading system is provided. The centrifuge loading system includes a staging platform containing bucket inserts, a weight scale coupled to the staging platform being operable to determine weight of each of the bucket inserts, a centrifuge adapted to receive the bucket inserts in bucket insert pairs, a robot operable to move an unprocessed sample container to one of the bucket inserts on the staging platform, and a controller operable to command the robot to carry out placement of the unprocessed sample container into a highest priority unoccupied receptacle location of a lowest combined weight bucket insert.

In another apparatus aspect, a loading apparatus is provided. The apparatus includes a staging platform containing at least two bucket inserts, a weight scale operable to determine a combined weight of each of the bucket inserts, a centrifuge configured to receive the bucket inserts in at least one bucket insert pair, a robot operable to insert an unprocessed sample container into one of the at least two bucket inserts, and a controller operable to command the robot to carry out placement of the unprocessed sample container into a highest priority unoccupied receptacle of a lowest combined weight bucket insert.

Still other aspects, features, and advantages of the present invention may be readily apparent from the following detailed description by illustrating a number of example embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

DETAILED DESCRIPTION

In current centrifuging systems, it is desired to load and unload centrifuge bucket inserts to and from centrifuge buckets concurrently to the operation of the centrifuge to efficiently utilize this resource.

Figure 1:
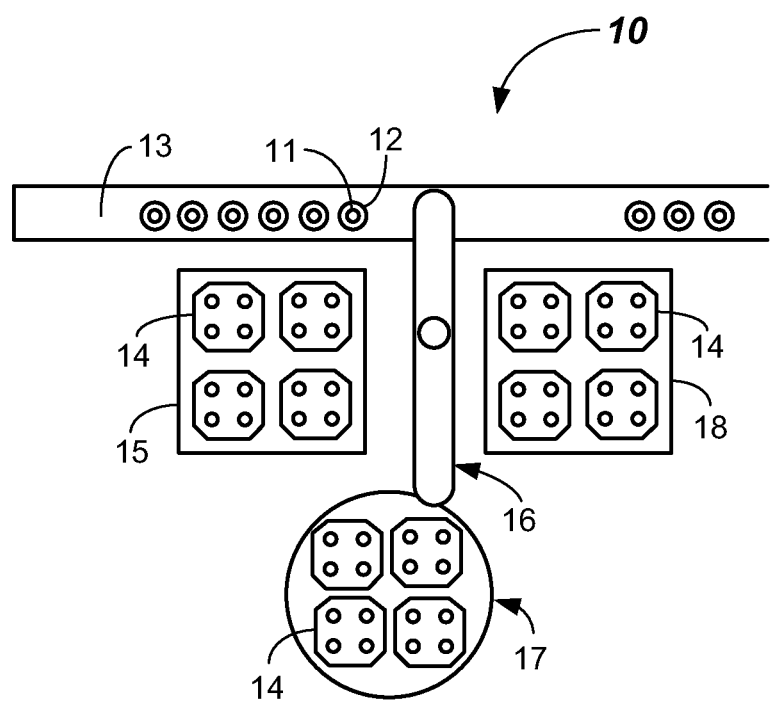
FIG. 1 is an illustration of an example centrifuge loading and unloading system according to the prior art.

Current centrifuge loading and unloading systems 10, as shown in FIG. 1, utilize an approach whereby the input processing and output processing of sample containers is physically segregated. In particular, centrifuge loading and unloading station 10, like those disclosed in U.S. Pat. No. 6,060,022 and U.S. Pat. No. 6,589,789, are adapted to remove a sample container 11 carried by a sample container carrier 12 from track 13 and to place individual sample containers 11 in a pattern into open receptacles (not shown for purposes of clarity) in a centrifuge bucket insert 14 disposed temporarily on a first bucket weighing and loading platform 15 (the input staging area).

Centrifuge loading and unloading station 10 is provided with a bucket transfer device 16 adapted to remove a centrifuge bucket insert 14 from first loading platform 15 and to place the centrifuge bucket insert 14 into centrifuge 17 for centrifuging. In order to avoid an unbalanced centrifuging condition, additional centrifuge bucket inserts 14 are loaded on the first loading platform 15 placed into centrifuge 17 so as to maintain an overall balanced load within centrifuge 17. Typically, centrifuge bucket inserts 14 are placed into centrifuge 17 in opposing pairs.

After centrifuging is complete, centrifuge loading and unloading station 10 utilizes bucket transfer device 16 to remove a centrifuge bucket insert 14 from centrifuge 17 one after another and to place each centrifuge bucket insert 14 onto a first bucket unloading platform 18 (an output staging area). For purposes of simplicity, only four sample containers 11 are illustrated in each centrifuge bucket insert 14, while in practice a larger number on the order of 10-20 sample containers 11 are typically placed into each centrifuge bucket insert 14.

Finally, bucket transfer device 16 is adapted to remove centrifuged sample containers 11 from bucket insert 14 disposed on first buck unloading platform 18 and to replace the now-centrifuged sample containers 11 into carriers 12 on track 13 for subsequent pre-analytical processing and/or for analysis. After all centrifuged sample containers 11 have been removed from a centrifuged bucket insert 14, empty centrifuge bucket insert 14 moved from unloading platform 18 and onto the loading platform 15. This loading and unloading process is continued until all of the sample containers 11 in sample carriers 12 requiring some form of separation have been centrifuged and replaced onto conveyor track 13.

Prior to centrifuging, the centrifuge bucket inserts 14 may be weight balanced. Weight balancing according to the prior art involves adding dummy tubes or rearranging sample containers 11 to provide suitable balancing. However, such balancing operation takes time to accomplish. Any time the centrifuge is not processing sample containers 11 is a lost opportunity cost.

In view of the foregoing problems, embodiments of the present invention in one aspect provide methods, systems, and apparatus adapted and operational to load bucket inserts in a manner to achieve better balancing and substantially reduce or eliminate having to balance the bucket inserts after all the unprocessed sample containers are inserted therein. The system, apparatus and method may reduce the overall time it takes to load a batch of sample containers. In addition, time is saved by minimizing a number of robot motions (moves) as well as the distance traveled by the robot, thus minimizing wear of the components thereof.

Thus, in a first aspect, a method of loading a centrifuge is provided that includes determining a combined weight of each of the bucket inserts, and placing an unprocessed sample container into a highest priority unoccupied receptacle location of a lowest combined weight bucket insert.

These and other aspects and features of embodiments of the invention will be described with reference to FIGS. 2-4 herein.

Figure 2:
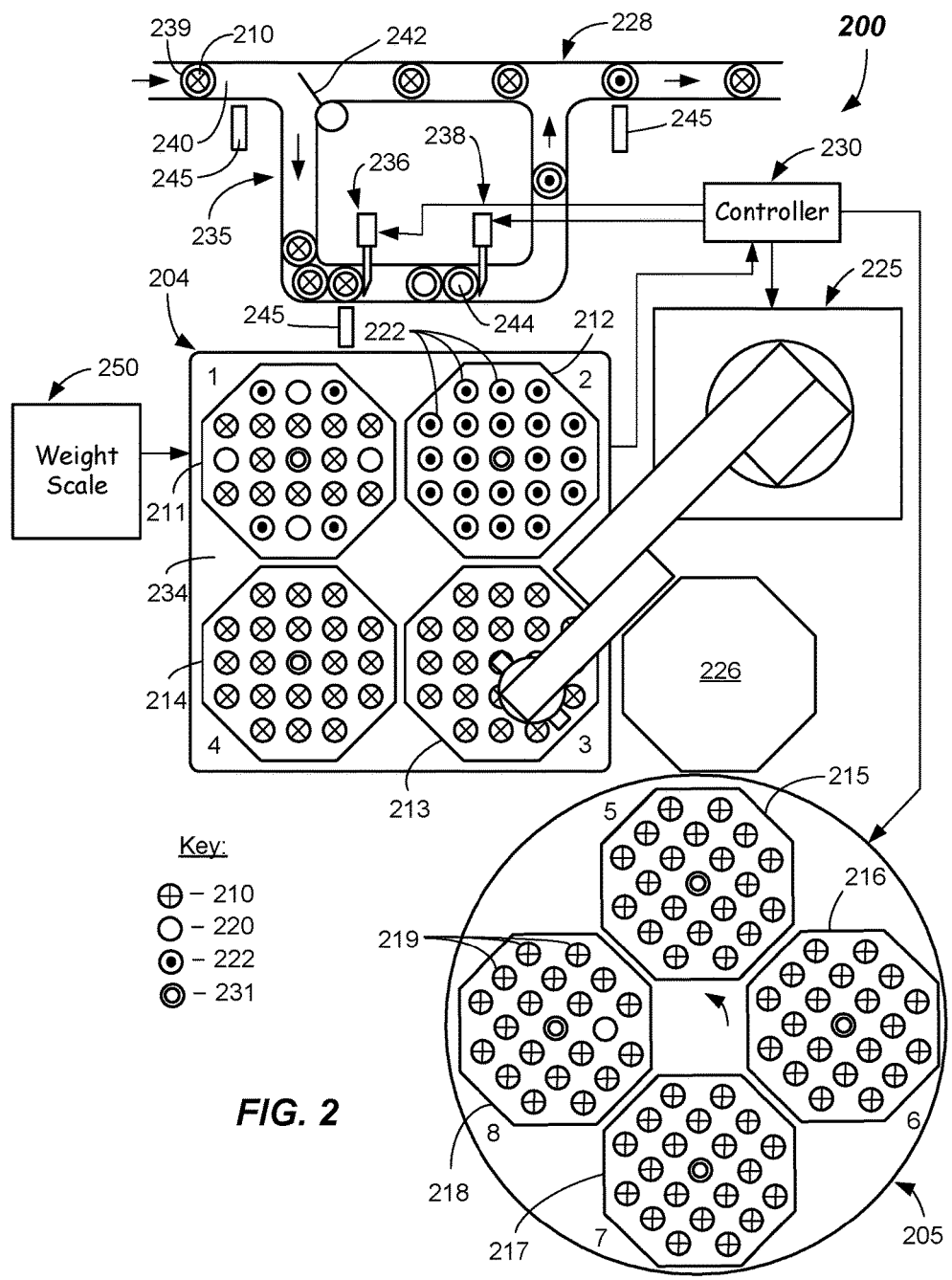
FIG. 2 illustrates a graphical diagram of a centrifuge loading system according to embodiments.

In accordance with a first embodiment of the invention, as best shown in FIG. 2, a centrifuge loading system 200 is described. The centrifuge loading system 200 may also accomplish unloading of a centrifuge. The centrifuge loading system 200 is useful for reducing a time to provide suitably balanced bucket inserts to a centrifuge, for example. In particular, the described embodiment includes a staging platform 204 containing multiple locations labeled 1, 2, 3, 4 that are adapted to support multiple inserts, such as bucket inserts 211-214. The staging platform 204 may be constructed of any suitable material and may be of any suitable shape to support the bucket inserts 211-214. The bucket inserts 211-214 may be substantially identical to one another and may be of the approximately the same weight. At least one of the bucket inserts 211-214 may be a common bucket insert (e.g., 211) as will be described later herein.

The staging platform 204 may be a platform adapted to receive the bucket inserts 211-214 and include a weight scale 250, which may be positioned underneath the platform 204 to provide a combined weight of the bucket inserts 211-214. The combined weight of each bucket insert is the weight of the bucket insert and contents (e.g., unprocessed sample containers 210). A weight of each of the bucket inserts 211-214 may be determined initially by removing and replacing each bucket insert from and to the platform 204. The weight of each bucket inserts 211-214 may be stored in a database in memory of a controller 230.

The system 200 further includes a centrifuge 205 having multiple locations such as buckets 5, 6, 7, 8 that are adapted to receive bucket inserts 215-218. The buckets 5-8 may be configured to have any shape that has receptacles 219 adapted to accept and position the bucket inserts 215-218. For example, the buckets 5-8 may be suspended from yoke assembly (not shown), as is conventional. The centrifuge 205 is adapted to separate various components of specimens provided therein. In particular, the centrifuge 205 may be a Hettich centrifuge available from Hettich Centrifuges of Beverly, Mass., which is adapted to receive bucket inserts 211-218 (sometimes referred to as "sample cassettes") into the buckets 5-8 which may be pivotally mounted to a yoke (not shown) of the centrifuge 205.

Bucket inserts 215-218 received into the buckets 5-8 may contain unprocessed sample containers 210, as shown. Unprocessed sample containers 210 are sample containers, such as blood collection tubes and the like, that contain a specimen (e.g., blood) to be centrifuged. Unprocessed sample containers 210 are labeled with a cross herein. Prior to centrifuging, all of the receptacles 219 (a few labeled) in the bucket inserts 215-218 may be full. In other embodiments, at least some receptacles 219 may be empty. Empty receptacles 220 are designated as O's herein. In any event, each of the bucket inserts will be weight balanced in accordance with a method embodiment of the invention.

As will be described in more detail below, the centrifuge loading method includes carrying out placement of the unprocessed sample containers based upon a combined weight of the bucket inserts and a schedule of priority containing the locations of priority positions (order ranked).

The system 200 further includes a robot 225 positioned adjacent to the staging platform 204 and a temporary storage location 226. The robot 225 may be operable as commanded to: 1) move unprocessed sample containers 210 to a bucket insert 211-214, 2) remove processed sample containers 222 from the bucket inserts 211-214, and 3) move the bucket inserts (e.g., 211-214) between the staging platform 204 and the buckets 5-8 of the centrifuge 205. Thus, the robot 225 functions to load and unload the bucket inserts 211-218. Additionally, the robot 225 may load and unload the unprocessed sample containers 210 and processed sample containers 222 to and from a conveyor system 228.

In addition, the system 200 includes a controller 230 operable to command and cause the robot 225 to carry out a sample container movement sequence. In particular, the sequence is adapted to move unprocessed sample containers 210 to a selected bucket insert (e.g., 211-214) at the staging platform 204 and place each unprocessed sample container 210 into a receptacle 219 in a specified manner. Additionally, the sequence may remove processed sample containers 222 from the bucket inserts (e.g., 211-214) at the staging platform 204. In some instances, a common bucket insert (e.g., 211) may contain both unprocessed sample containers 210 and processed sample containers 222 at a same time.

The robot 225 may be any suitable robot adapted to move the unprocessed sample containers 210 from the conveyor system 228 to the staging platform 204, and processed sample containers 222 to the conveyor system 228 from the staging platform 204. The same robot 225 may also move the bucket inserts 211-214 to the buckets 5-8 of the centrifuge 205, remove the bucket inserts 215-218 from the centrifuge 205, and also transport the bucket inserts 211-214 (or bucket inserts 215-218) to the temporary storage location 226. The bucket inserts 211-214 may be moved by grasping a central post 231 on each bucket insert 211-218. The central post 231 is designated herein as an unfilled circle within a circle. Other suitable means for moving the bucket inserts 211-218 may be provided.

The robot 225 may be a multi-arm robot, such as a selective compliance articulated robot arm (SCARA) robot, gantry robot, or the like. Other types of robots may be used. The robot 225 may include one or more shoulder, elbow, or wrist elements to accomplish three-dimensional motion thereof. In some embodiments, the robot may be an R-Theta robot adapted to move an end effector in an R direction as well as rotate about a fixed point in Theta (rotational direction). The robot 225 end effector may be a finger set adapted to grasp the processed and unprocessed sample containers 210, 222, and also the central post 231 on the bucket inserts 211-218. The means for moving the components (e.g., arms and end effectors) of the robot 225 may include any suitable conventional motion-producing mechanism, such as one or more stepper motors, servo motors, pneumatic or hydraulic motors, electric motors, or the like. Furthermore, drive systems including chains, guides, pulleys and belt arrangements, gear or worm drives, rack and pinions, or other conventional drive components may be utilized to cause the motion of the components of the robot 225.

The conveyor system 228 may be any suitable conveyor capable of moving the sample containers 210, 222 to and from the staging platform 204. Conveyor system 228 may include a moving belt or track, for example. Other gates and reader systems may be used on the conveyor system 228 to deflect the carriers and the sample containers 210, 222 to and from a main lane of the conveyor system 228 and track a location of the sample containers 210, 222 entering and exiting from the staging area 204.

Figure 3A:
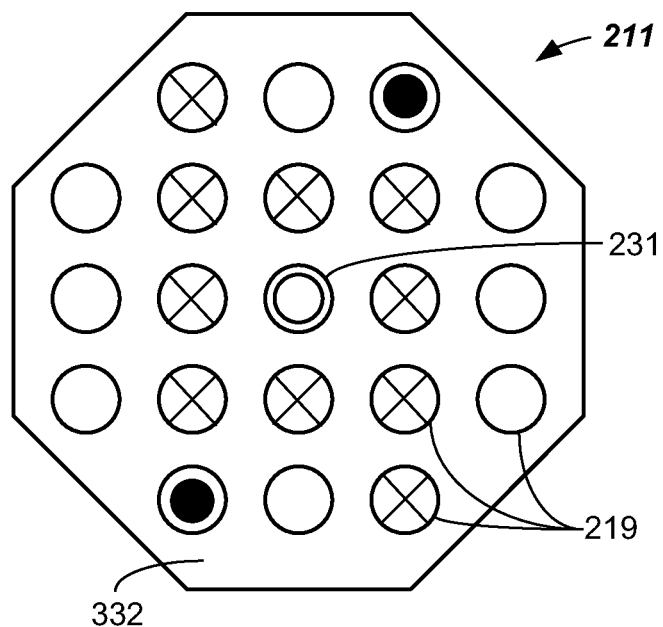
FIGS. 3A and 3B illustrate top and side plan views, respectively, of a bucket insert containing sample containers according to embodiments.
Figure 3B:
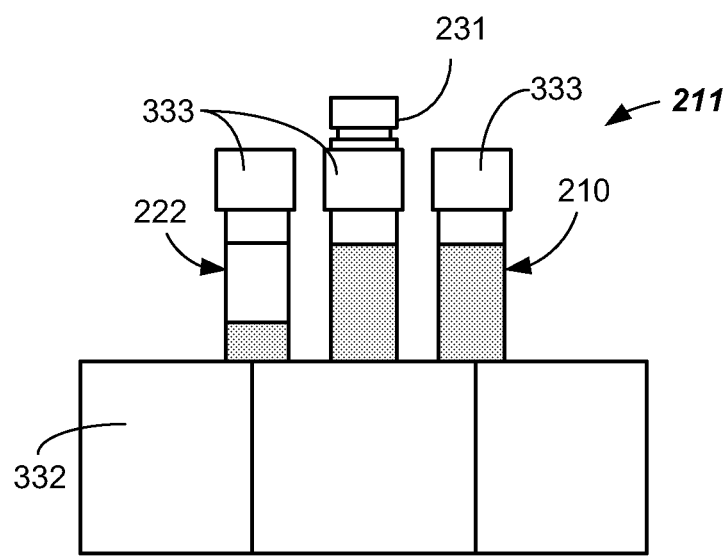
Figure 3C:
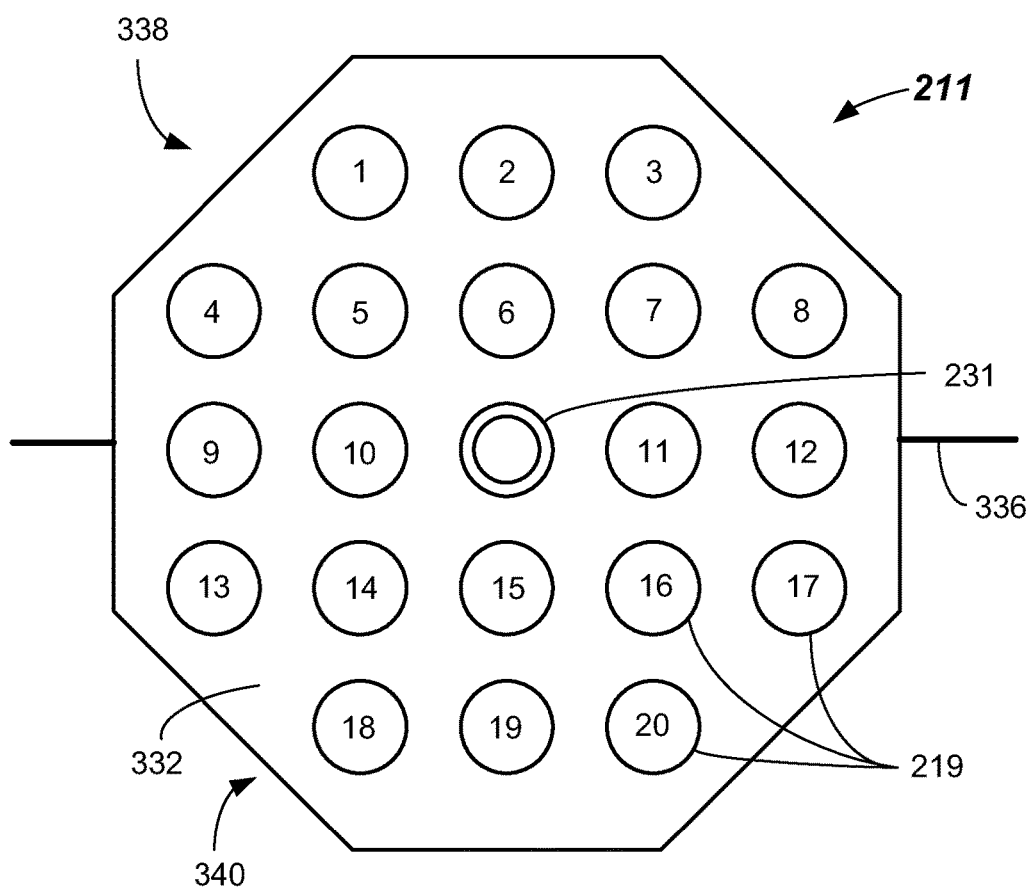
FIG. 3C illustrates a top plan view, respectively, of a bucket insert labeled receptacles according to embodiments.
Figure 4:
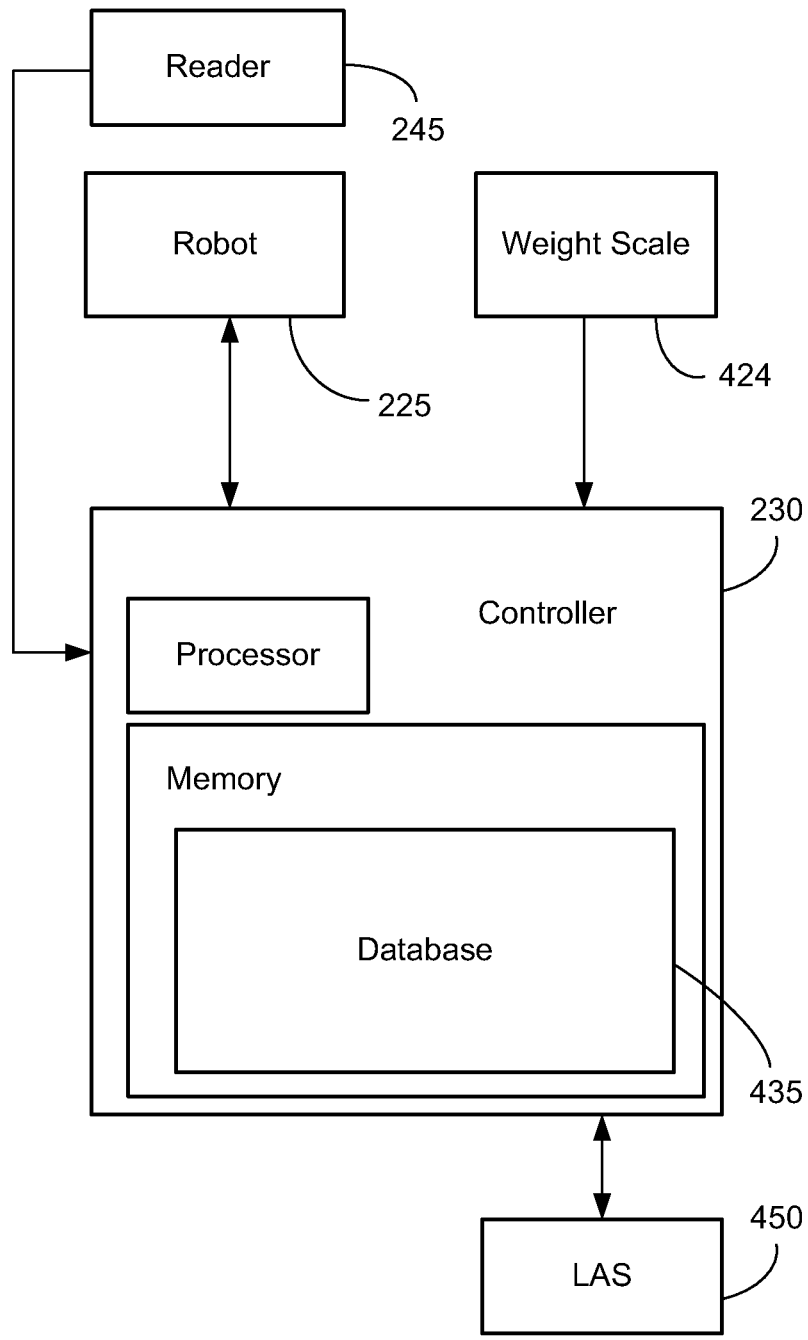
FIG. 4 illustrates a graphical diagram of a loading system to embodiments.

A representative bucket insert is shown in FIGS. 3A through 3C and includes a body 332 having the plurality of receptacles 219 adapted to receive the sample containers 210, 222, and the central post 231 extending upward from the body 332 and configured to be grasped by the robot 225. The bucket insert 211 may be a common bucket insert in some embodiments and may contain unprocessed sample containers 210 having blood therein, processed sample containers 222 having been centrifuged to separate the blood components, and may contain at least some empty receptacles 220. All of the sample containers 210, 222 may be capped with a conventional cap 333. FIG. 3C illustrates numbering of the various receptacles 219 to facilitate a detailed explanation of the loading sequence to be carried out in accordance with one or more embodiments of the invention.

After processing (e.g., centrifuging) a batch has taken place, such as by spinning the bucket inserts 211-214 containing unprocessed sample containers 210 in the centrifuge 205 at a sufficient speed (e.g., between about 3000 RPM and 4000 RPM) for a sufficient time (e.g., between about 8 min and about 12 min), for example, the sample containers now contain processed specimens (e.g., that have been separated into their constituent components of whole blood and serum portions, and possibly a separation layer) and are now designated as processed sample containers 222. Processed sample containers 222 are designated herein by having a dot therein. For example, location 2 at the staging area 204 is shown including a bucket insert 212 having processed sample containers 222 that have been removed from the centrifuge 205 in a previous batch.

Again referring to FIG. 2, the staging platform 204 may include a tray 234 which may be coupled to and supported by a weighing mechanism such as a weight scale 250 that is adapted to measure the combined weight of each of the bucket inserts 211-214 resting on the tray 234 and provide a signal to the controller 230 thereof. The weight scale 250 also is used to determine a weight of each unprocessed sample containers 210 as the unprocessed sample container 210 is added into a bucket insert 211-214. The controller 230 may include a suitable processor and memory including a sufficiently-sized database adapted to record the combined weight (the cumulative weight of the bucket insert and its instantaneous contents of unprocessed sample containers 210) of each bucket insert 211-214, an identity of the bucket insert 211-214 receiving the unprocessed sample container 210 and processed sample containers 222, and the assigned location (e.g., 1-20 as shown in FIG. 3C) of each receptacle 219 in the bucket inserts 211-214 as well as bucket inserts 215-218 and their contents.

Each location may be given an indicia or name in the tracking database such that at any point in time, the population (whether containing an unprocessed or processed sample container 210, 222 or an empty receptacle 220) of each location in each bucket insert 211-218 is exactly known. As the bucket inserts 211-218 progress through the system 200 and are, in sequence, transferred to the temporary storage area 226, from the staging area 204, to the centrifuge 205, and back to the staging area 204, the orientation of each of the bucket inserts 211-218 may be retained so that the exact location of the receptacles 219 in the sample containers 210, 222 in is known at all times. As the processed sample containers 222 are removed, that information is used to update the tracking database. Thus, for each of the bucket inserts 211-218 the identity, type of sample container, and weight of sample container in each receptacle 219 is known and tracked. A location of empty receptacles 220 of the common bucket insert (and/or in other bucket inserts) is also be tracked. Moreover, a weight of each of the bucket inserts 211-218 is known at all times.

In accordance with one aspect, a number of the common bucket inserts 211-214 at the staging platform 204 may be one, two, three, or four. The number of common bucket inserts may diminish as the bucket inserts are filled with unprocessed sample containers 210 in preparation for loading the next batch. A common bucket insert is defined herein as a bucket insert that contains both unprocessed sample containers 210 and processed sample containers 222 at a same time. The common insert may also contain empty receptacles 220.

As a batch has completed processing at the centrifuge 205, the robot 225 may unload the bucket inserts 215-218 one by one. One sample container movement sequence that may be carried out by the robot 225 caused by commands from the controller 230 is shown in Table 1 below.

TABLE 1

Bucket Insert Movement Sequence

| Movement | Time (s) |
|---|---|
| 1 to Temp Storage Location | 9 |
| 5 to 1 | 9 |
| 2 to 5 | 9 |
| 6 to 2 | 9 |
| 3 to 6 | 9 |
| 7 to 3 | 8 |
| 4 to 7 | 10 |
| 8 to 4 | 9 |
| Temp Storage Location to 8 | 7 |

To start the centrifuge bucket loading and unloading process, one bucket insert that is ready for processing is placed at the temporary storage location 226. Following this, the bucket insert movement sequence may be followed whereby a processed bucket insert (e.g., bucket insert 215) is removed from the centrifuge 205 and placed into the staging area 204 and an unprocessed bucket insert (e.g., bucket insert 212) is placed in the bucket just vacated (e.g., bucket 5). At the end of a batch, or intermittently during the bucket insert movement sequence, loading and unloading from the one or more common bucket inserts (e.g., 211) may be accomplished. The goal is to provide one or more unprocessed bucket inserts (e.g., 213, 214) as soon as possible so that it may take the place of a processed bucket insert when a batch has completed centrifuging. Bucket inserts containing STAT specimens may be loaded first to the centrifuge 205. Likewise, a processed sample container 222 containing a STAT specimen may be first removed from the centrifuge 205 and may be immediately loaded to the loading station 238 before loading processed sample containers containing non-STAT specimens and before loading a bucket insert having unprocessed sample containers 210 to the bucket just vacated.

During the loading process, a balancing process may be enacted in accordance with one or more embodiments of the invention. The balancing process ensures the various bucket inserts 215-218 at buckets 5-8 of the centrifuge 205 are appropriately weight balanced as they are loaded to the centrifuge 205. In accordance with one or more embodiments of the invention, the various bucket inserts 211-214 at the staging platform 204 may be loaded in a manner so as to approximately balance the weight of each bucket inserts 211-214. The weight balancing may be achieved in a manner described below.

In accordance with one or more embodiments, a weight of each of the bucket inserts 211-214 is first determined. This may be done at startup, before each new batch is started, or at periodic time increments, for example. A weight of each of the bucket inserts 211-218 is determined (when empty) and is recorded in the database 435. From this data, a bucket insert 211-214 currently residing on the staging platform 204 having a lowest weight is identified (a lowest weight bucket insert), such as by comparing the weights one to the other. An unprocessed sample container 210 is than placed in an empty receptacle 220 of the lowest weight bucket insert 211-214. In accordance with embodiments of the invention, the receptacle location (1-20) that receives the unprocessed sample container is a highest priority position selected from a schedule of priorities, i.e., the highest priority location that is available. The schedule of priorities may be as shown in Table 2 below.

TABLE 2

Schedule of Priorities

| Highest Priority | | | |
|---|---|---|---|
| BI 1-6 | BI 1-15 | BI 13-6 | BI 3-15 |
| BI 2-6 | BI 2-15 | BI 4-6 | BI 4-15 |
| BI 1-10 | BI 1-11 | BI 3-10 | BI 3-11 |
| BI 2-10 | BI 2-11 | BI 4-10 | BI 4-11 |
| BI 1-5 | BI 1-16 | BI 3-5 | BI 3-16 |
| BI 2-5 | BI 2-16 | BI 4-5 | BI 4-16 |
| BI 1-7 | BI 1-14 | BI 3-7 | BI 3-14 |
| BI 2-7 | BI 2-14 | BI 4-7 | BI 4-14 |
| BI 1-9 | BI 1-12 | BI 3-9 | BI 3-12 |
| BI 2-9 | BI 2-12 | BI 4-9 | BI 4-19 |
| BI 1-4 | BI 1-17 | BI 3-4 | BI 3-17 |
| BI 2-4 | BI 2-17 | BI 4-4 | BI 4-17 |
| BI 1-8 | BI 1-13 | BI 3-8 | BI 3-13 |
| BI 2-8 | BI 2-13 | BI 4-8 | BI 4-13 |
| BI 1-2 | BI 1-19 | BI 3-2 | BI 3-19 |
| BI 2-2 | BI 2-19 | BI 4-2 | BI 4-19 |
| Lowest Priority | | | |

In accordance with one aspect, the highest priority positions for each bucket insert are offset from a centerline 336, but radially closest thereto (the radial direction is a direction being co-extensive or co-parallel with a line connecting receptacle locations 2 and 19, for example). The absolute highest priority positions in a bucket insert (e.g., 211) as shown in FIG. 3C are at a centermost position (in a width dimension), wherein the width dimension is along a direction co-extensive or co-parallel with a line connecting receptacle locations 9-12. Receptacle positions 6 and 15 are examples of highest priority positions in each bucket insert 211-214, for example. As used in Table 2, B1 refers to the lowest weight insert whereas B4 refers to the highest weight bucket insert, thus in terms of initial weight the weights from lowest to highest are B1, B2, B3 and B4. The centerline 336 is also co-aligned vertically when first installed in a bucket 5-8 of the centrifuge 205 with the yoke hinge point. As used herein, a first side 338 is on a first side of the centerline 336 and a second side 340 is on a second side that is opposite the first side 338.

As can be seen, the next highest priority positions are positioned along the centerline 336 of the bucket insert 211-214 and may be widthwise closest to the center, i.e., next to the post 231. Receptacle positions 10 and 11 are examples thereof. A next highest priority positions may be radially offset from the centerline 336 and offset widthwise from the width center. Examples are receptacle positions 5 and 16 and 7 and 14. A next highest priority position may be along the centerline 336. Examples are receptacle positions 9 and 12. A next highest priority position may be radially offset and offset widthwise. Examples are receptacle positions 4 and 17, and 8 and 13. A next highest priority position may be further radially offset (e.g., in a next row out from the centerline 336) and closest to a center widthwise. Examples are receptacle positions 2 and 19. The lowest priority positions may be further radially offset from the centerline 336 and offset widthwise from the width center. Examples are receptacle positions 1 and 20 and 3 and 18.

Thus, as a general rule, the bucket inserts 211-214 will be loaded according to a schedule of priorities of receptacle locations. The priorities (ranked highest to lowest) may be:
1) radially offset and closest to centermost width,
2) on the centerline 336 and closest to centermost width,
3) radially offset and offset widthwise,
4) on centerline 336 and further offset widthwise,
5) radially offset and further offset widthwise,
6) further radially offset and closest to center widthwise, and
7) further radially offset and further offset widthwise.

Other placement priority schedules may be used to balance the bucket inserts 211-214 for weight as between each other, but also to balance the bucket inserts 211-214 side to side (between first side 338 and second side 340).

Each time the controller 230 commands the robot 225 to load a bucket insert 211-214 with an unprocessed sample container 210, the controller 230 determines the then-existing lowest weight bucket insert BI1-BI4 assigned to the bucket inserts 211-214. The robot 225 will then insert the unprocessed sample container 210 into the highest priority empty receptacle 220 in the lowest weight bucket insert BI1-BI4. The highest priority empty receptacle 220 is determined via a schedule of priorities.

In some instances, such as when the bucket insert is a fully empty bucket insert, the highest priority position is available and the unprocessed sample container 210 will be inserted therein. If not, the unprocessed sample container 210 will be inserted into the next highest priority empty receptacle 220 according to the priority schedule being used. After insertion, the change in cumulative weight is measured by the weight scale 424, and the cumulative weight of the bucket insert (BI1) is updated in the database 435. The receptacle location may also be noted. Other indicia may be noted and cross referenced in the database 435, such as by reading a barcode or other indicia on the unprocessed sample container 210 with a reader 245 coupled to the controller 230. The controller 230 may be linked to a automated laboratory system (LAS) 450 and may communicate status of various sample containers 210, 222 within the system 200.

For example, it may be determined that the sample is a STAT sample either by reading a barcode on the unprocessed sample container 210 with a reader or by communication with the LAS 450, and may be loaded into a particular bucket insert reserved for STAT samples, which may be first removed after centrifuging the batch. As unprocessed sample containers 210 continue to be loaded, the cumulative weight of each bucket insert 211-214 is determined and updated and the highest priority receptacle locations are first populated each time in the bucket insert (BI1) having the lowest instantaneous cumulative weight according to a priority schedule. In this manner, the bucket inserts are loaded so as to be of approximately equal weight, but also so that the first side 338 and the second side 340 are also approximately weight balanced. Thus, advantageously, not only is each bucket insert 211-214 approximately weight balanced with respect to the other bucket inserts, each bucket insert is also approximately weight balanced, side to side.

In some embodiments, a running weight of each side 238, 240 of each bucket insert 211-214 may be monitored by the controller 230. When two placement options are available in a lowest cumulative weight bucket insert (BI1) of the same priority or only slightly different priority, placement on the lowest weight side may be carried out. The weights of the first and second sides 338, 340 of each bucket insert 411-414 may be constantly updated in the database 435.

As the bucket inserts 211-214 become completely full or filled to a level of fullness acceptable to the process, such that all of the bucket inserts 411-414 are ready for loading to the centrifuge 205 as a new batch, the controller 230 may evaluate and compare the instantaneous cumulative weights of each of the bucket inserts 211-214, and rank order them from lightest to heaviest (BI1-BI4). The bucket inserts 211-214 may then be matched in pairs. The two lightest bucket inserts (BI1 and BI2) may be matched, and the two heaviest (BI3 and BI4) may be matched as pairs. The matched pairs may then be positioned in buckets 5-8 across from each other in the centrifuge 205.

Once matched, and preferably before moving them, the weight differences between the pairs are compared against preset threshold differences. If the differences are too large, then dummy weights may be added to the lowest weight bucket insert of the pair. This will then balance the pairs to be within the preset thresholds. If already within the preset threshold, no further weighting is carried out. Optionally, the position of one or more of the unprocessed sample containers may be moved from one of a pair to the other of the pair to balance the pair within the preset threshold.

Again referring to FIG. 2, one sample container loading and unloading apparatus and process that may be used with the loading system 200 includes a loading/unloading lane 235 on the conveyor system 228. The loading/unloading lane 235 may include an unloading station 236 and a loading station 238. Loading station 238 may be located downstream of the unloading station 236. The unloading station 236 provides a source of unprocessed sample containers 210 to be centrifuged at the centrifuge 205. Unloading station 236 may receive carriers 239 (e.g., pucks) containing unprocessed sample containers 210 that have been diverted from a main lane 240 by a diverter mechanism 242. Any suitable diverter mechanism 242 may be used that may either diverts carriers 239 or leave the carriers 239 to continue along on the main lane 240, as desired. For example, in some instances, carriers 239 may be allowed to travel to another centrifuge or another processing location further downstream. The diverter mechanism 242 may have two positions; one for diverting, and one that allows the carrier 239 to continue on along the main lane 240.

During an unloading and unloading process, a processed sample container 222 may be picked up from a bucket insert (e.g., 212 that has just been unloaded from a centrifuged batch. In particular, in order to free up a highest priority position, the robot will first remove the processed sample container from the highest priority position of the lowest weight bucket insert (having the weight of the processed sample containers 222 not counted) according to the priority schedule being used. The processed sample container 222 may be picked up by an end effector of the robot 225. The end effector may be an opposed set of gripper fingers, for example. The gripper fingers may be driven to open and close by a suitable end effector drive apparatus, such as a servo motor or the like. Any suitable mechanism for causing gripping action may be used.

The processed sample container 222 may be carried directly to the loading station 238 by the robot 225 and placed in an empty carrier 244 that is staged at the loading station 238. Once loaded, the carrier 244 may be released from station 238 by any suitable release mechanism and may move towards and reenter the main lane 240. Once on the main line 240, the processed sample container 222 may travel to other stations along the track for further analysis or testing. One or more additional readers 245, such as a barcode reader or the like may be provided at suitable positions along the main lane 240, or even at the loading/unloading lane 235 to enable tracking of a location of the various sample containers 210, 222 entering and exiting the loading system 200 at the loading/unloading lane 235. This information may be sent to an automated laboratory system (LAS) 450 for tracking a location and status of the sample containers 210, 222.

Once the robot 225 has delivered the processed sample container 222, the robot end effector may move directly to the unloading station 236 and may unload an unprocessed sample container 210 from a carrier 239 stationed at the unloading station 236. This unprocessed sample container 210 may be inserted into the previously emptied empty receptacle 220, which is the highest priority position of the lowest weight bucket insert (not counting the weight of the processed sample containers 222 therein). This fills the space and thus converts the bucket insert 212 into a common bucket insert containing both an unprocessed sample container 210 and processed sample containers 222 at a same time. However, the presence of sample containers has no real bearing on the efficacy of the balancing process as there are treated as though they are not there and they are removed one by one from the highest priority positions thus allowing unprocessed sample containers to replace them.

This unload/load sample container movement sequence will continue until all of the processed sample containers 222 are unloaded to the loading station 238 and all the bucket inserts 211-214 are reloaded with unprocessed sample containers 210 from the unloading station 236 to a desired level of fullness. In some instances, the bucket inserts 211-214 will be full, and in others, some empty receptacles 220 will be included. The bucket inserts (211-214) will again matched in pairs as described herein. They may be moved to the centrifuge 205 by the robot 225 to be centrifuged in a next batch after checking whether the balance will fall within the preset threshold. If out of the threshold balancing may take place as described above. Side to side balance of each bucket insert may also be checked, and corrected if needed.

Figure 5:
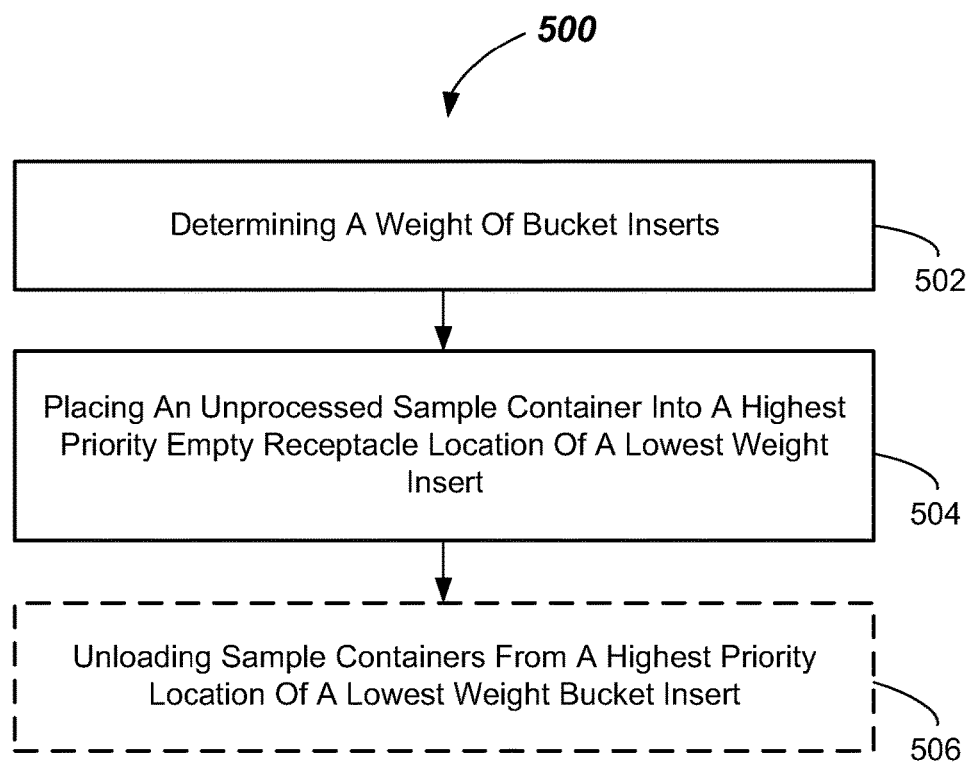
FIG. 5 illustrates a flowchart of a method of loading a centrifuge according to embodiments.

One embodiment of a method of loading a centrifuge will now be described with reference to FIG. 5. The method 500 includes, in 502, determining a weight of bucket inserts (e.g., bucket inserts 211-214). More or less numbers of bucket inserts than those shown may be used. For example two or more, or even more that four may be used. For example, staging platform 204 may have two, three, four, five, or even six bucket inserts thereat.

The method 500 also includes, in 504, placing an unprocessed a sample container (e.g., unprocessed sample container 210) into a highest priority empty receptacle 220 of a lowest weigh bucket insert (e.g., BI1). The sample containers may be unprocessed sample containers 210 before centrifuging. The number of buckets (e.g., 5-8) may be the same as or less than the number of bucket inserts (e.g., 211-214) at the staging platform 204. However, in one or more embodiments, the number of buckets is equal to the number of bucket inserts at the staging platform 204. For example, the system 200 may include four bucket inserts (e.g., bucket inserts (211-214) at the staging platform 204, and four bucket inserts (e.g., bucket inserts 215-218) at the centrifuge 205. Thus, in one embodiment, eight or less bucket inserts are included in the loading system 200.

Additionally, the method 500 may optionally include, in 506, unloading sample containers (e.g., processed sample containers 222) from a highest priority location of a lowest weight bucket insert of the multiple bucket inserts at the staging platform 204. The lowest weight bucket is determined by not counting the weight of the processed samples containers therein. This frees up priority receptacle locations for insertion of the next unprocessed sample container 210. The priority schedule may be as described herein.

While the invention is susceptible to various modifications and alternative forms, specific system and apparatus embodiments and methods thereof have been shown by way of example in the drawings and are described in detail herein. It should be understood, however, that it is not intended to limit the invention to the particular systems, apparatus, or methods disclosed but, to the contrary, the intention is to cover all modifications, equivalents, and alternatives falling within the scope of the invention.

What is claimed is:

1. A method of loading a centrifuge, comprising:
disposing a plurality of bucket inserts on a tray of a staging area;
operating a weight scale disposed under, and coupled to, the tray of the staging area to weigh the plurality of bucket inserts; and
placing an unprocessed sample container into a highest priority unoccupied receptacle location of a lowest weight bucket insert.

2. The method of claim 1, further comprising:
updating a weight of the lowest weight bucket insert with the added unprocessed sample container placed in a database.

3. The method of claim 1, further comprising placing the unprocessed sample container into a lowest weight side of the lowest weight bucket insert.

4. The method of claim 3, further comprising updating a weight of the sides of the bucket inserts in a database.

5. The method of claim 3, further comprising evaluating a weight of all the bucket inserts, of the plurality of bucket inserts, that are ready for centrifuging.

6. The method of claim 5, further comprising:
matching the two heaviest bucket inserts of the plurality of bucket inserts as a first bucket insert pair; and
matching the two lightest bucket inserts of the plurality of bucket inserts as a second bucket insert pair;
wherein the first bucket insert pair and the second bucket insert pair are to be loaded into the centrifuge.

7. The method of claim 6, further comprising:
checking if a first weight difference of the first bucket insert pair and a second weight difference of the second bucket insert pair are within a weight difference threshold.

8. The method of claim 7, further comprising:
adjusting a weight of one or more of the first bucket insert pair responsive to the first bucket insert pair being outside of the weight difference threshold; and
adjusting a weight of one or more of the second bucket insert pair responsive to the second bucket insert pair being outside of the weight difference threshold.

9. The method of claim 8, wherein the adjusting comprises:
adjusting the weight of one or more of the first bucket insert pair that is outside of the weight difference threshold by
rearranging unprocessed sample containers, or
adding dummy weights.

10. The method of claim 9, further comprising not adjusting the weight of one or more of the first bucket insert pair in more than 50% of batches.

11. The method of claim 7, further comprising:
checking a weight of sides of each of the bucket inserts of the first bucket insert pairs, and
rearranging unprocessed sample containers in sides of the first bucket insert pairs if a weight of each of the sides are not within a predefined side weight difference threshold.

12. A centrifuge loading system, comprising:
a staging platform configured to receive one or more bucket inserts;
one or more bucket inserts disposed on the staging platform;
a weight scale disposed under, and coupled to, the staging platform and configured to determine weight of each bucket insert of the one or more bucket inserts disposed on the staging platform;
a centrifuge adapted to receive one or more bucket insert pairs;
a robot operable to move an unprocessed sample container to one of the bucket inserts on the staging platform; and
a controller operable to command the robot to carry out placement of the unprocessed sample container into a highest priority unoccupied receptacle location of a lowest weight bucket insert.

13. The centrifuge loading system of claim 12, wherein the robot is operable to move the bucket inserts of the one or more bucket inserts between the staging platform and a corresponding one or more buckets of the centrifuge.

14. The centrifuge loading system of claim 12, wherein the controller determines a lowest weight side of the lowest weight bucket insert and the robot is operable to place the unprocessed sample container into the lowest weight side of the lowest weight bucket insert.

15. The centrifuge loading system of claim 12, wherein the controller determines a weight of each of the bucket inserts that is ready for centrifuging, matches the two heaviest bucket inserts and the two lightest bucket inserts as bucket insert pairs, and commands loading of the two heaviest bucket inserts and the two lightest bucket inserts as bucket insert pairs into the centrifuge.

16. The centrifuge loading system of claim 12, wherein the controller:
checks a weight of sides of each of the bucket inserts of the bucket insert pairs, and
commands the robot to rearrange the sides of the bucket insert pairs if a weight of each of the sides is not within a predefined side weight difference threshold.

17. A centrifuge loading apparatus, comprising:
a staging platform having at least two bucket inserts disposed thereon;
a weight scale disposed under, and coupled to, the staging platform, and configured to determine a weight of each of the bucket inserts disposed on the staging platform;
a centrifuge configured to receive the bucket inserts in at least one bucket insert pair;
a robot operable to insert an unprocessed sample container into one of the at least two bucket inserts; and
a controller operable to command the robot to carry out placement of the unprocessed sample container into a highest priority unoccupied receptacle of a lowest combined weight bucket insert.

18. The centrifuge loading apparatus of claim 17, wherein the controller determines placement of the unprocessed sample container into a side of the lowest combined weight bucket insert having a lowest side weight.

19. The centrifuge loading apparatus of claim 17, wherein the controller determines a highest priority unoccupied receptacle according to a schedule of priorities.

20. The centrifuge loading apparatus of claim 19, wherein the schedule of priorities includes, ranked highest priority to lowest priority:
positions radially offset from a centerline of a bucket insert, but closest to a center of a width of the bucket insert,
positions on the centerline of the bucket insert, and
positions radially offset from a centerline of a bucket insert, and offset in a width direction from a center of a width of the bucket insert.

* * * * *